United States Patent [19]

Muhlemann et al.

[11] Patent Number: 4,522,806
[45] Date of Patent: Jun. 11, 1985

[54] ORAL COMPOSITIONS FOR HEXETIDINE AND ZINC SALTS FOR THE SYNERGISTIC INHIBITION OF DENTAL PLAQUE

[75] Inventors: Hans R. Muhlemann; Ulrich P. Saxer, both of Zurich, Switzerland

[73] Assignee: Lever Brothers Company, New York, N.Y.

[21] Appl. No.: 563,011

[22] Filed: Dec. 19, 1983

Related U.S. Application Data

[63] Continuation of Ser. No. 309,050, Oct. 6, 1981, abandoned.

[30] Foreign Application Priority Data

Oct. 10, 1980 [GB] United Kingdom ............... 8032743

[51] Int. Cl.$^3$ .................. A61K 7/18; A61K 7/22
[52] U.S. Cl. ...................... 424/52; 424/54; 424/145
[58] Field of Search ............ 424/54, 52, 145

[56] References Cited

U.S. PATENT DOCUMENTS

| | | | |
|---|---|---|---|
| 3,095,356 | 6/1963 | Moss | 167/93 |
| 3,622,662 | 11/1971 | Roberts | 424/54 |
| 3,985,537 | 10/1976 | Harrison et al. | 424/54 |
| 3,989,814 | 11/1976 | Cordon et al. | 424/57 |
| 4,022,880 | 5/1977 | Vinson et al. | 424/54 |
| 4,100,269 | 7/1978 | Pader | 424/54 |
| 4,138,477 | 2/1979 | Gaffar | 424/52 |
| 4,141,968 | 2/1979 | Kunz et al. | 424/55 |
| 4,142,050 | 2/1979 | Kunz et al. | 424/54 |
| 4,170,634 | 10/1979 | Cordon et al. | 424/49 |
| 4,187,288 | 2/1980 | Cordon et al. | 424/49 |

FOREIGN PATENT DOCUMENTS

| | | |
|---|---|---|
| 771768 | 4/1957 | United Kingdom . |
| 1284544 | 8/1972 | United Kingdom . |
| 1284545 | 8/1972 | United Kingdom . |
| 1284546 | 8/1972 | United Kingdom . |
| 1310374 | 3/1973 | United Kingdom . |
| 1461896 | 1/1977 | United Kingdom . |
| 1533634 | 11/1978 | United Kingdom . |
| 2001526A | 2/1979 | United Kingdom . |
| 2084870 | 4/1982 | United Kingdom . |

*Primary Examiner*—Shep K. Rose
*Attorney, Agent, or Firm*—Lynne Darcy; James J. Farrell

[57] ABSTRACT

Oral compositions, such as mouthwashes, sprays, gels, oral foams, toothpastes and the like which include a combination of an antibacterial pyrimidine amine base, especially hexetidine, plus one or several zinc salts. This combination inhibits the formation of dental plaque synergistically, without staining the teeth.

8 Claims, No Drawings

ORAL COMPOSITIONS FOR HEXETIDINE AND ZINC SALTS FOR THE SYNERGISTIC INHIBITION OF DENTAL PLAQUE

This is a continuation application of Ser. No. 309,050, filed Oct. 6, 1981, now abandoned.

FIELD OF THE INVENTION

This invention relates generally to oral compositions and more particularly concerns a composition which inhibits the formation of dental plaque without staining the teeth.

BACKGROUND OF THE INVENTION

The term "oral compositions" is used herein to designate products which in the ordinary course of usage are retained in the oral cavity for a time sufficient to contact substantially all of the dental and gingival surfaces, but which are not ingested. Such products include, for example, mouthwashes, sprays, dental gels, oral foams and dentifrices.

Dental plaque is a dense, tenacious deposit of oral bacteria. Calcification (mineralization) of dental plaque results in dental calculus. Calculus formation depends on the presence of plaque.

Plaque forms and grows on the surface of teeth, preferentially in the cervical, interdental and fissure areas and also on dental restorations, crowns, bridges and dentures. Plaque is the obligate cause of dental caries, and plaque and calculus are the causes of inflammatory destruction of the tooth-supporting gingival and periodontal structures (periodontitis).

A wide variety of chemical agents have been suggested to retard plaque formation and the resulting plaque diseases. Mechanical removal of plaque is attempted with oral hygiene measures, but average toothbrushing only partially results in plaque removal. Therefore, the additional use of chemical antibacterials inhibiting plaque formation in inaccessible dental areas is indicated. Germicides which have been proposed include phenolic compounds, halogenated bis-phenols (e.g. hexachlorophene), organic mercurials, hydroxyquinolines, iodine esters of hydroxybenzoic acids, chloramine T, and surface active compounds (detergents) among others. These germicides are excellent laboratory disinfectants but are relatively poor in vivo plaque inhibitors in contrast to cationic organic antibacterial agents, such as water soluble salts of cetylpyridinium, of quaternary ammonium bases (benzalkonium chloride), of alkylamines (fluoride of N,N,N'-tris-(2-hydroxyethyl)-N'-octadecyl-1,3-diaminopropane) and of cationic amidines, and water soluble salts of chlorhexidines, such as Hibitane, Alexidine and Vantocil.

The effect on plaque formation of mouthwashes used daily and containing cetylpyridinium chloride (Carter, H. G., Barnes, G. P.: *Effects of three mouthwashes on existing dental plaque accumulations.* J Prev Dent 2, 10, 1975; Ciancio, S. G., Mather, M. L., Bunnell, H. L.: *Effect of a quaternary ammonium type mouthrinse on formed plaque.* J Dent Res 54 A, Abstract 585, 1975), cetylpyridinium chloride plus a quaternary ammonium base (Domiphen bromide) (Barnes, G. P., Roberts, D. W., Katz, R. V., Woolridge, E. D.: *Effects of two cetylpyridinium chloride-containing mouthwashes on bacterial plaque.* J Periodontol 47, 419, 1976) or benzethonium chloride alone (Volpe, A. R., Kupczak, L. J., Brant, J. H., King, W. J., Kestenbaum, R. C., Schlissel, H. J.: *Antimicrobial control of bacterial plaque and calculus and the effects of these agents on oral flora.* J Dent Res 48, 832, 1969) is relatively modest when compared with amidines. This is evident when comparing mouthwashes containing chlorhexidine digluconate with other mouthwash antibacterials (Gjermo, P., Baastad, K. L., Rolla, G.: *The plaque inhibiting capacity of 11 antibacterial compounds.* J Peridont Res 5, 102, 1970; Muhlemann, H. R., Hulss, D., Steiner, E.: *Antimicrobial rinses and proximal plaque on removable gold crowns.* Helv Odont Acta 17, 89, 1973; and Bergenholtz, A., Hanstrom L.: *The plaque-inhibiting effect of hexetidine (Oraldene ®)-mouthwash compared to that of chlorhexidine.* Community Dent Oral Epidemiol 2, 70, 1974.) Unfortunately, mouthrinsing with amidines will rapidly produce a cosmetically unacceptable brown stain on the teeth (Flotra, L., Gjermo, P., Rolla, G., Waerhaug, J.: *Side effects of chlorhexidine mouthwashes.* Scand J Dent Res 79, 119, 1971). Cationic detergents and amidines have also been found to irritate the oral mucosa even when used at recommended therapeutic concentrations in rinsing solutions (Flotra, L.: *Different modes of chlorhexidine application and related local side effects.* J Periodont Res 8, Supp. 12, 41, 1973).

The antiplaque properties of metal ions were mentioned as early as 1940 (Hanke, M. T.: *Studies on the local factors in dental caries. I. Destruction of plaque and retardation of bacterial growth in the oral cavity.* JADA 27, 379, 1940). U.S. Pat. No. 593,485 refers to zinc phenolsulfonate as bactericide. The use of zinc oxide or zinc phosphate for the stabilization of dental creams is described in U.S. Pat. No. 3,622,662. Zinc oxide and zinc sulphate are described in U.S. Pat. No. 3,624,199 for the same purpose. Effervescent antiplaque tablets containing zinc chloride are described in U.S. Pat. No. 3,888,976. Pader (U.S. Pat. No. 4,082,841) reported the anticalculus effect of zinc ions. A composition reducing the formation of dental calculus is reported in German Pat. No. 2,203,379.

Various zinc salts have been studied in clinical trials to determine their antiplaque potential when used in mouthwashes, but the results were conflicting. A zinc chloride solution at 1000 ppm zinc concentration was reported in one study to be effective (Skjorland, K., Gjermo, P., Rolla, G.: *Effect of some polyvalent cations on plaque formation in vivo.* Scand J Dent Res 86, 103, 1978), and in another trial to be totally ineffective (Compton, F. H., Beagrie, G. S.: *Inhibitory effect of benzethonium and zinc chloride mouthrinses on human dental plaque and gingivitis.* J Clin Periodontol 2, 33, 1975). Soluble zinc citrate displays a small plaque inhibitory action at zinc concentrations of 600 ppm (Addy, M., Richards, J., Williams, G.: *Effects of a zinc citrate mouthwash on dental plaque and salivary bacteria.* J Clin Periodontol 7, 309, 1980) and 1000 ppm (Waler, S. M., Rolla, G.: *Plaque inhibiting effect of combinations of chlorhexidine and the metal ions zinc and tin. A preliminary report.* Acta Odontol Scand 38, 201, 1980), respectively. Zinc chloride rinses (Zn=1000 ppm) clearly depresses calculus formation (Schmid, M. O., Schait, A., Muhlemann, H. R.: *Effect of a zinc chloride mouthrinse on calculus deposits formed on foils.* Helv Odont Acta 18, 22, 1974), and zinc chloride bound to carboxysulphate- and phosphate groups were reported to have deodorant properties. Zinc chloride complexed to polymers of carboxyl sulfate and phosphate groups prevents or controls mouth odor.

In recent years mechanisms of plaque inhibiting properties of metal ions have become increasingly evident (White, S. T., Taylor, P. P.: *The effect of stannous fluoride on plaque scores.* J Dent Res 58, 1850, 1979; Svatun, B., Gjermo, P., Eriksen, H. M., Rolla, G: *A comparison of the plaque-inhibiting effect of stannous fluoride and chlorhexidine.* Acta Odontol Scand 35, 247, 1977; Hock J., Tinanoff, N.: *Resolution of gingivitis in dogs following topical applications of 0.4% stannous fluoride and toothbrushing.* J Dent Res 58, 1652, 1979). Plaque apparently is only loosely adsorbed on the enamel in the presence of metal ions. Metal ions also interfere with the metabolic (enzymatic) activity of bacteria, particularly with acid formation from dietary carbohydrates. From among ions of silver, zinc, magnesium, tin and aluminum, stannous ions seem to possess the highest antiplaque activity (Svatun, B.: *Plaque-inhibiting effect of dentifrices containing stannous fluoride.* Acta Odontol Scand 36, 205, 1978; Gjermo, P., Rolla, G.: *Plaque inhibition by antibacterial dentifrices.* Scand J Dent Res 78, 464, 1970). Unfortunately, it is difficult to prevent hydrolysis and precipitate formation in mouthwashes containing water-soluble tin salts (Shannon, I. L. and Gibson, W. A.: *Shelf life of aqueous solutions of stannous fluoride.* USA School of Aerospace Medicine, Brooks Air Force Base, Texas, SAM-TDR-63-104). In addition, stannous fluoride is known to stain teeth. Yellowish discoloration is not known to occur with the use of zinc ions, such as zinc fluoride, zinc acetate and zinc chloride.

A mouthwash containing a 0.22% zinc chloride (Lavoris) has been marketed in the U.S. for many years. There is general agreement that zinc salts have a beneficial adstringent effect on inflamed oral mucosae and that they are modest plaque inhibitors.

Antiplaque and anticalculus effects have been claimed for zinc ions combined with tetradecylamine (U.S. Pat. No. 4,146,607), with glycine (British Patent Application GB No. 2,052,978 A), and with enzymes (U.S. Pat. No. 4,082,841). The combination of zinc salts with amidines (EPC Patent Application No. 0,026,252) is reported to prevent tooth discolorations without loss of amidine antiplaque action.

Antiplaque effects of oral rinses containing zinc salts and antibacterials have been reported in U.S. Pat. No. 4,022,880. The combination of zinc with antibacterials has been described in U.S. Pat. No. 4,022,880. Claims are only made for additive effects: "Our discovery concerns the co-action of zinc ions and an antibacterial agent, rather than a well defined synergistic property" ( column 4 of U.S. Pat. No. 4,022,880). The antibacterials listed in U.S. Pat. No. 4,022,880 are amidines, quaternary ammonium bases, phenolics a.s.o., but not pyrimidine amine bases nor hexetidine specifically. In addition many zinc salts are referred to, but not zinc fluoride. However, some scientific investigations have shown possible incompatibilities between solutions of zinc salts and quaternary ammonium bases. In another trial, zinc acetate combined with chlorhexidine digluconate was found to be slightly but not significantly superior in antiplaque action when compared with chlorhexidine alone (Waler, S. M., Rolla, G., supra).

Hexetidine, a saturated pyrimidine derivate, the analytical profile of which was recently reported, (Satzinger, G., Herrmann, W., Zimmermann, F.: *Analytisches Profil des Rein-Hexetidins.* Drug Research 25, 1849, 1975. (Godecke AG, Freiburg i.Br., West Germany)) has been used in mouthrinses for over 20 years. The chemical formula of Hexetidine is:

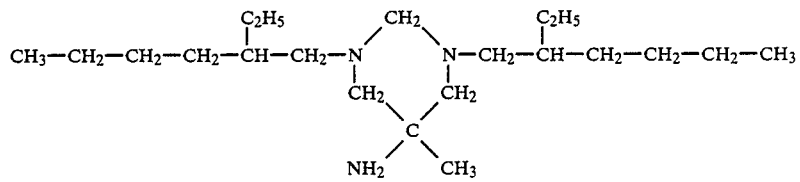

1,3-bis(2-ethylhexyl)hexahydro-5-methyl-5-pyrimidineamine.

Well known marketed mouthwashes containing 0.1 to 0.2 percent hexetidine are Drossadine, Hexoral, Hextril, Oraldene, Sterisol. They have been mainly recommended as pre- and postoperative astringent oral antiseptics and for the elimination of unpleasant breath.

Antiseptic oral effects of hexetidine, its depressive action on inflammed oral mucosae and its deodorant effects in the oral cavity were for the first time extensively reported in 1958 at a Symposium on Hexetidine, Northwestern University, Chicago, Ill. (Godecke Publication report on Hexoral ®; Report of Warner-Chilcott on Hextril ®).

The plaque inhibiting action of 0.1 percent hexetidine alone is similar to zinc salt solutions, is relatively moderate, and is more than 50 percent smaller than 0.2 percent chlorhexidine digluconate rinses (Muhlemann, H. R., Hulss, D., Steiner, E.: *Antimicrobial rinses and proximal plaque on removable gold crowns.* Helv Odont Act 17, 89, 1973; Muhlemann, H. R.: *Auf dem Weg zum sauberen Zahn?* SWISS DENT 2, No. 1-2, 7, 1981; Muhlemann, H. R., Saxer, U. P.: *Plaque inhibition by rinsing solutions containing aminefluoride, hexetidine and zinc ions.* Preprinted Abstract No. 17, ORCA-Congress 1981, Erfurt, DDR; Saxer, U. P., Muhlemann, H. R.: *Plaque-inhibiting effect of zinc ions and fluoride, hexetidine and their combinations.* Preprinted Abstract No. 18, ORCA-Congress 1981, Erfurt DDR). In addition, there are indications that retention of hexetidine in the oral cavity after rinsing, and subsequent antiglycolytic effects in plaque are less pronounced than in the case of chlorhexidine (Hefti, A., Widmer, B.: *Reduktion des Keimpegels in der Mundhohle vor zahnarztlichen Behandlungen durch Mundwasser und Mundantiseptika.* Schweiz Mschr Zahnheilk 90, 73, 1980) and amine chloride (Breitenmoser, Th.: *The antiglycolytic action on dental plaque of amine chloride.* Helv Odont Acta 19, 13, 1975), respectively.

Plaque and calculus reduction studies with combinations of zinc salts and a water-insoluble pyrimidine base hexitidine have hitherto not been described in theliterature.

SUMMARY OF THE INVENTION

It is an object of this invention to provide a novel oral antiplaque composition based on the combination of a water-insoluble pyrimidine base, hexetidine, plus one or several zinc salts and with a nonionic solubilizer (emulgator), and with optionally soluble fluoride salts.

The word "combination" is intended to mean either: the simultaneous use of the two agents zinc and hexetidine in one oral composition, such as a zinc-hexetidine toothpaste, or a mouthwash containing zinc plus hexetidine; or the immediate successive use of two different oral compositions, one containing hexetidine the other a zinc salt, as for example, the brushing of teeth with a toothpaste containing a zinc salt and the subsequent rinsing with a mouthwash containing hexetidine, or vice versa.

It has been discovered that zinc fluoride dissolved and emulgated at a physiological pH together with hexetidine in an alcohol containing aqueous mouthwash have a pronounced synergistic antiplaque action in animal caries tests, clinical experiments and microbiological media. Clinical plaque reduction is similar to or may exceed that produced by chlorhexidine, and without staining the teeth.

This invention encompasses novel oral compositions which contain hexetidine in combination with zinc salts and which are stable and which are used at a physiological oral pH. The combination of hexetidine with zinc salts results in a highly synergistic statistically significant inhibition of oral microorganisms and of plaque formation on teeth and dental restorations which improves oral hygiene and simultaneously depresses the inflammation of gums (gingivitis). The use of the zinc-hexetidine-combination at eight hour intervals almost totally inhibits growth of plaque without irritating the oral mucosae and without staining the teeth.

The antibacterial effect of the zinc-hexetidine-combination is specific. Replacement of zinc by other metal ions or replacement of hexetidine by amidines, quaternary ammonium bases a.s.o. will annihilate the antibacterial synergism of the zinc-hexetidine-combination at low concentrations.

Preferably the composition according to this invention contains one of the following combinations: hexetidine and zinc fluoride, or hexetidine, zinc fluoride plus other zinc salts, or hexetidine plus zinc fluoride and other zinc salts, or hexetidine and non-fluoride zinc salts. Also, a water-insoluble pyrimidine amine base preferably is rendered soluble and is emulgated at a physiological pH, preferably in a nonionic emulgator (Cremophor) and ethanol. The antiplaque zinc-hexetidine-combination is preferably used with both agents included in one oral composition. Alternatively, the two agents each may be in a separate composition and used successively one after the other.

These and other objects of the invention will become apparent from a further and more detailed description of the invention to follow.

DETAILED DESCRIPTION OF THE INVENTION

Experimental evaluation was made of the inhibition of plaque formation in (a) animal experiments; (b) clinical investigations; and (c) microbiological media.

(a) Animal Experimentation

Four groups of 13 twenty one day old Osborne-Mendel rats each were inoculated orally with a suspension of Streptococcus mutans OMZ 176 and Actinomyces viscosus Ny 1. Subsequently the cariogenic sucrose containing diet 2000 a was offered ad libitum for 3 weeks. The solutions specified in Table I were applied to the rat molars 3 times per day. At the end of the experiment the extent of plaque formed on the molars was evaluated with a scoring system. The findings are summarized in Table I.

TABLE I

The effects on plaque formation of various solutions containing zinc ions and hexetidine in Osborne-Mendel rats fed the cariogenic diet 2000 a

| | Topically applied compounds | Abbreviated designation | Average extent of plaque formed on molars+, PU |
|---|---|---|---|
| A | 250 ppm F as NaF | H$_2$O Control | 3.5 |
| B | 250 ppm F as NaF 750 ppm F. Hexetidine | Hex 750 ppm | 3.4 |
| C | 250 ppm F from ZnF$_2$ 750 ppm Zn from ZnF$_2$ + Zinc acetate | Zinc 75 ppm | 2.2 |
| D | 250 ppm F from ZnF$_2$ 750 ppm Zn from ZnF$_2$ + Zinc acetate 750 ppm Hexetidine | Hex 750 ppm + Zinc 750 ppm | 1.1 |

+theoretical maximum value = 4.0
*P$_F$ significances

Inhibition (1.1 PU) of plaque formation was synergistic and significantly greatest in the case where zinc fluoride/zinc acetate plus hexetidine were combined in one solution (treatment D). Hexetidine alone was without effect (3.4 PU) and zinc fluoride was inhibitory (2.2 PU).

(b) Clinical Investigations

Six female dental hygiene students who ranged in age from 20 to 26 years old, and who were known from previous investigations to be heavy plaque formers when consuming sucrose candies frequently, participated in a clinical test of four mouthwash solutions. Prior to each of the four consecutive 7-day-rinsing periods, the subjects had their teeth cleaned, pumiced and polished professionally. The volunteers then were randomly assigned to one of the 4 anti-plaque rinsing treatments listed below. For ethical considerations a neutral water control rinse was omitted. The subjects had to rinse 3 times a day (twice under supervision) for 30 seconds and had to refrain from tooth brushing and other mechanical hygiene procedures.

The four rinsing treatments utilized are as follows: (1) a solution containing 0.1 percent chlorhexidine digluconate freshly prepared from Plak Out Liquid. Plak Out Liquid is a 10 percent chlorhexidine concentrate (HAWE, Gentilino-Lugano, Switzerland), and 4 drops in 10 ml of water provides a 0.1% solution; (2) a solution containing 0.1 percent hexetidine plus zinc fluoride (ZnF$_2$) at 215 ppm zinc and 250 ppm fluorine (adapted with sodium fluoride) concentrations; (3) a solution containing N,N,N'-tris-(2-hydroxyethyl)-N'-octadecyl-1,3-diaminopropane dihydrofluoride (amine fluoride, compound 297) at 250 ppm fluorine plus zinc fluoride (ZnF$_2$) at 215 ppm zinc; and (4) a solution containing amine fluoride 297 (250 ppm fluorine) plus stannous fluoride (SnF$_2$) at 250 ppm fluorine.

Lycasin 8055 (Roquette Freres, Lestrem, France) was added to all treatments. It is a sweetening agent containing mainly maltitol, sorbitol and hydrogenated dextrines. Each object rinsed with one of the four experimental solutions which was assigned at random. There were no set time intervals between the treatments. The study was performed double blind. The rate of plaque formation was documented at the end of each experimental period by standardized color photographs of the teeth stained with Displac. The extent of plaque formation was determined planimetrically using projected Kodachrome slides. The findings are summarized in Table II.

TABLE II

The effect of four different mouthwash solutions, one containing chlorhexidine, another hexetidine and zinc fluoride ($ZnF_2$), another amine fluoride 297* and $ZnF_2$, and another amine fluoride 297 and $SnF_2$, on plaque formation in 6 subjects abstaining from mechanical oral hygiene measures during 4 consecutive 7 day rinsing periods. Averages of planimetric units PU ± standard deviation.

| Rinsing Solution | Positive control chlorhexidine | Hexetidine $ZnF_2$ | Amine Fluoride 297* + $ZnF_2$ | Amine Fluoride 297* + + $SnF_2$ |
|---|---|---|---|---|
| 7-day extent ofpaquel,PU | 188 ± 90 | 30 ± 9 | 101 ± 54 | 61 ± 22 |
| Theoretical amount of plaque formed per day | 26.9 | 4.3 | 14.4 | 8.7 |

*N,N,N'—tris-(2-hydroxyethyl)-N'—octadecyl-1,3-diaminopropane.2HF

Inhibition of plaque formation with the hexetidine-$ZnF_2$ combination was significantly superior to the chlorhexidine rinse ($P_t<0.01$), and to the rinses containing amine fluoride+$SnF_2$($P_t<0.05$) and amine fluoride+$ZnF_2$($P_t<0.05$). When rinsing with 0.1 percent chlorhexidine, plaque at an average of 26.9 PU per day was formed (Table II). The same volunteers who in a previous and similar investigation rinsed with water containing Lycasin 8055 had produced plaque at an average of 50.2 PU per day, suggesting, therefore, the relatively strong antiplaque activity of the 0.1 percent chlorhexidine rinse (Plak Out) in the present study (26.9 PU/day). No staining of teeth resulted from the treatment with hexetidine+$ZnF_2$. A yellowish stain, however, was produced by the chlorhexidine rinse. All of the rinsing solutions showed stability and remained clear over the treatment periods and for several months thereafter.

In a second clinical test with 10 dental hygiene students, the antiplaque effects of zinc fluoride, hexetidine, and $ZnF_2$ plus hexetidine were tested. The rinsing solutions were: (1) control (NaF, 250 ppm fluorine); (2) $ZnF_2$ (250 ppm fluorine, 750 ppm zinc); (3) Hexetidine (750 ppm) plus NaF (250 ppm); and (4) $ZnF_2$ (250 ppm fluorine, 750 ppm zinc) plus hexetidine (750 ppm) pH 5.9. The solutions were combined with aromatics. They were well tasting and non-irritative to oral mucosae. The experimental procedures were similar to those reported for the previous experiment. At the beginning of the four one-week-rinsing periods, the 10 female dental hygiene students were given a professional tooth cleaning. They then refrained from mechanical oral hygiene procedures and rinsed 3 times per day (twice under supervision) with 10 ml for 30 sec. The test solutions were assigned at random. The plaque reductions observed in the double blind study are summarized in Table III.

TABLE III

Average plaque indices ± standard deviation and average planimetric units in 10 volunteers refraining from tooth brushing and other mechanical oral hygiene procedures but rinsing during four one-week test periods with one of four hexetidine-and zinc fluoride solution.

|  | PI I Plaque Index (Silness-Loe) | Percentage of vestibular tooth surfaces covered with plaque (PU) |
|---|---|---|
| Control | 2.58 ± 0.28 | 33.4 ± 16.57 |
| $ZnF_2$ | 2.16 ± 0.38 | 23.2 ± 14.44 |
| Hexetidine | 2.11 ± 0.72 | 17.4 ± 8.07 |
| Zn + Hexetidine | 0.77 ± 0.55 | 3.5 ± 2.17 |

The results show the synergistic and highly significant plaque inhibition by the zinc-hexetidine-mouthwash.

(c) Microbiological Investigation

The synergistic antibacterial effect of the zinc hexetidine-combination is clearly evident in microbiological investigations. Twenty-four hour growth and acid production of Streptococcus mutans cultured in a glucose-containing synthetic FMC-broth are totally inhibited by zinc acetate alone at a minimal concentration of 40 ppm zinc, and by hexetidine alone at 0.4 ppm. The combination of both agents in the broth results in total bacterial inhibition at a concentration of 4.0 ppm zinc and 0.08 ppm hexetidine. Zinc or hexetidine are without antibacterial effects at these low concentrations.

The synergistic antibacterial effect can also be observed if zinc and hexetidine, are used sequentially on washed streptococcal cultures, either the zinc being applied first and subsequentally hexetidine being applied, or the hexetidine being applied first and then the zinc being applied. The synergistic inhibition of plaque microorganisms with the zinc-hexetidine-combination is specific. Other metal ions, as for example, stannous ions, combined with hexetidine, or other antibacterials combined with zinc only cause additive antibacterial effects.

In summary, the synergistic and specific antiplaque effect of the disclosed zinc hexetidine combination has been demonstrated in a rat caries test and in two independent clinical plaque studies, using organoleptically acceptable mouth rinses. Synergistic inhibition was also observed in microbiological laboratory investigations. Oral compositions with derivates of pyrimidine amine bases or of hexetidine plus zinc salts dissolved in the emulgator Cremophor are included in the present invention.

Components of exemplary oral compositions in accordance with the present invention are given in the following examples:

EXAMPLE I

Mouthwash

| Hexetidine | | 0.1 |
|---|---|---|
| Zinc fluoride | | 0.1 |
| Sodium fluoride | | 0.05 |
| Glycerol | | 5.0 |
| Cremophor EL | | 0.25 |
| Ethanol | | 10.0 |
| Polyoxyethylen-sorbitanmonoleate | | 0.1 |
| Aromatics, saccharin | | 0.15 |
| Water | ad | 100.0 |

EXAMPLE II

Mouthwash

| | | |
|---|---|---|
| Hexetidine | | 0.2 |
| Zinc citrate | | 0.15 |
| Glycerol | | 5.0 |
| Cremophor EL | | 0.25 |
| Ethanol | | 10.0 |
| Aromatics, saccharin | | 0.1 |
| Water | ad | 100.0 |

EXAMPLE III

Spray

| | | |
|---|---|---|
| Hexetidine | | 0.2 |
| Zinc acetate | | 0.1 |
| Potassium fluoride | | 0.05 |
| Cremophor EL | | 0.5 |
| Ethanol | | 15.0 |
| Aromatics, saccharin | | 0.2 |
| Water | ad | 100.0 |
| Propellant | | |

EXAMPLE IV

Dental Gel

| | | |
|---|---|---|
| Hexetidine | | 0.2 |
| Hydroxyethylcellulose | | 3.0 |
| Zinc fluoride | | 0.2 |
| Sodium fluoride | | 2.1 |
| Negion | | 0.5 |
| Cremophor EL | | 1.0 |
| Flavor, coloring agents | | 0.5 |
| Water | ad | 100.0 |

EXAMPLE V

Clear Dental Gel

| | | |
|---|---|---|
| Hexetidine | | 0.1 |
| Zinc acetate | | 0.1 |
| Sodium fluoride | | 0.2 |
| Sorbitol (70% solution) | | 50.0 |
| Glycerol | | 27.0 |
| Aerosil D 200 | | 5.0 |
| Sident 3 | | 15.0 |
| Cremophor EL | | 0.3 |
| Sweetener, color, flavor | | 2.0 |
| Water | ad | 100.0 |

EXAMPLE VI

Toothpaste

| | | |
|---|---|---|
| Hexetidine | | 0.3 |
| Zinc fluoride | | 0.1 |
| Sodium fluoride | | 0.1 |
| Guar gum | | 1.5 |
| Syloid | | 12.5 |
| Aerosil | | 2.0 |
| Glycerol | | 30.0 |
| Cremophor EL | | 0.5 |
| Aromatics | | 1.5 |
| Water | ad | 100.0 |

EXAMPLE VII

Lozenges

| | | |
|---|---|---|
| Hexetidine | | 0.001 |
| Zinc fluoride | | 0.003 |
| CMC | | 0.1 |
| Silica | ad | 1.0 |

EXAMPLE VIII

Zinc and hexetidine can also be combined using two different oral compositions, as for example, toothbrushing with a toothpaste of Example VI, which does not contain zinc and then subsequently rinsing with a mouthwash of Example I which does not contain hexetidine.

The names Hibitane, Alexidine, Vantocil, Domiphen bromide, Lavoris, Drossadine, Hexoral, Hextril, Oraldene, Sterisol, Lycasin, Cremophor, Plak Out and Displac are trademarks.

In view of the above description, it is likely that modifications and improvements will occur to those skilled in the art which are within the scope of this invention and which is defined solely in the following claims.

What is claimed:

1. An oral composition for inhibiting the formation of dental plaque comprising about 0.08 to about 3000 ppm w/w of hexetidine and zinc in cationic and cationizable form in a total quantity of about 4.0 to about 1265 ppm w/w.

2. The oral composition of claim 1 which comprises about 750 to about 3000 ppm w/w of hexetidine and zinc in cationic and cationizable form in a total quantity of about 215 to about 1265 ppm w/w.

3. The oral composition of claim 1 which further comprises a nonionic emulsifying agent.

4. The oral composition of claim 1 wherein the cationic and cationizable zinc is associated with anions selected from the group consisting of acetate, citrate, fluoride and mixtures thereof.

5. The oral composition of claim 1 in the form of a mouthwash.

6. The oral composition of claim 1 in the form of a spray.

7. The oral composition of claim 1 in the form of an oral foam.

8. The oral composition of claim 1 in the form of a lozenge.

* * * * *